United States Patent [19]

Patel

[11] 4,195,058
[45] Mar. 25, 1980

[54] VAPOR PERMEATION TIME-TEMPERATURE INDICATOR

[75] Inventor: Gordhanbhai N. Patel, Morris Plains, N.J.

[73] Assignee: Allied Chemical Corporation, Morris Township, Morris County, N.J.

[21] Appl. No.: 938,175

[22] Filed: Aug. 30, 1978

[51] Int. Cl.² ............................................. G01N 21/06
[52] U.S. Cl. ................................... 422/56; 23/230 R; 116/206; 422/58
[58] Field of Search ................ 23/230 R; 422/56, 57, 422/86; 116/114 AM, 114 V; 73/358

[56] References Cited

U.S. PATENT DOCUMENTS

| | | | |
|---|---|---|---|
| 3,501,297 | 3/1970 | Cremeans | 96/48 |
| 3,615,719 | 10/1971 | Michel et al. | 73/358 |
| 3,768,976 | 10/1973 | Hu et al. | 116/114 V |
| 3,844,718 | 10/1974 | Cohen | 23/253 TP |
| 3,999,946 | 12/1976 | Patel et al. | 23/253 TP |
| 4,042,336 | 8/1977 | Larsson | 73/358 |

Primary Examiner—R. E. Serwin
Attorney, Agent, or Firm—Robert J. North; Gerhard H. Fuchs

[57] ABSTRACT

An improved time-temperature indicator (t-T indicator) is described which is useful for monitoring the shelf lives of various perishable articles. The device is constructed of a vapor-permeable barrier positioned between a vapor and a liquid indicator, both housed in a vapor-impermeable container. The device is activated just prior to the monitoring period by providing vapor to the container, as for example, by rupturing a solvent-filled frangible reservoir. The liquid indicator, containing a polydiacetylene, upon contact with the vapor or condensed vapor produces a visual color response, and the vapor must permeate through the vapor-permeable barrier before contacting the liquid indicator, thus creating a characteristic induction period before a color response occurs. Color response occurs substantially simultaneously over the entire observable surface of the liquid indicator upon contact of the liquid indicator with the vapor. The time required for the color response to occur in the device is a function of the temperature and time. The induction period can be varied by the thickness and type of material of construction used for the vapor-permeable barrier, the nature of the vapor and the nature of the liquid indicator employed.

10 Claims, 6 Drawing Figures

VAPOR PERMEATION TIME-TEMPERATURE INDICATOR

BACKGROUND OF THE INVENTION

1. Field of the Invention

This invention relates to a device for monitoring time-temperature histories in which a vapor is allowed to contact a liquid polydiacetylene indicator resulting in a color response, by permeating through a vapor-permeable barrier, whereby a color response occurs only after a definite characteristic induction period.

2. Brief Description of the Prior Art

A host of perishable products such as frozen foods, blood, vaccines and the like require a means for monitoring time-temperature shelf life histories.

Various indicators have been developed in the prior art to meet this need with varying success.

Indicators are known that use a liquid or liquid vapor for activating a color response indicating that a predetermined shelf life has expired. For example, U.S. Pat. No. 3,844,718 discloses a defrost indicator which is activated by contact of water vapor with a water-soluble ink supported on a hygroscopic substrate.

U.S. Pat. No. 3,768,976 discloses a t-T indicator that depends upon the rate of permeation of gaseous oxygen through a polymer envelope containing an aqueous solution of a red redox dye. Upon oxidation, the red dye turns colorless, indicating that the perishable has been exposed to too high a temperature for too long a time. U.S. Pat. No. 3,615,719 discloses a temperature indicator in which a frozen liquid is separated from an indicating layer by a liquid-soluble barrier. When the frozen liquid thaws, a time delay is introduced by the rate of dissolution of the liquid soluble barrier. Only upon dissolution of this barrier does color indication occur.

U.S. Pat. No. 3,501,297 discloses a mixture of diacetylenes, capable of being converted by contact with warm ethanol vapors to a red color. However, such a color change by itself, is insufficient to suggest application as a practical time-temperature history indicator, since the color change may simply indicate that a particular temperature has been exceeded, without an indication either of the length of time that temperature has been exceeded or of the time-averaged exposure at higher temperatures.

U.S. application Ser. No. 911,629 (Patel to Allied Chemical, 1978) described a device for measuring time-temperature histories of an article in which a vapor is allowed to permeate through a vapor-permeable barrier to contact a solid indicator thus producing a color response as a function of the time and temperature. However, the induction periods and total lifetimes at room temperature are generally short, e.g. about one minute to several days and devices with longer extended induction times are needed for monitoring articles having relatively long shelf lives.

U.S. Pat. No. 4,042,336 (1977) describes a device for monitoring time-temperature histories comprising a gas generating means, an indicator means supported on a wick and a rate controlling means for transmission of the generated gas to the indicator means in which it is possible to alter the time span over which the device is functional by incorporating into the wick a quantifier reactive with said gas. However, the device requires a quantifier as an integral part of the indicator system and does not mention or suggest the use of polydiacetylenes as the colorindicating material.

SUMMARY OF THE INVENTION

We have unexpectedly found that a relatively longer characteristic induction period can be created prior to the occurrence of a color response in a device containing a vapor which contacts an indicator to produce a color response after permeating through a vapor-permeable barrier by utilizing a liquid indicator comprising a polydiacetylene indicating compound in solution rather than a solid indicator alone. The induction period can selectively be varied by the nature of the vapor and liquid indicator.

In accordance with this invention there is provided in a device for monitoring the time-temperature history of an article including:

(a) a closed vapor-impermeable container;

(b) at least one vapor-permeable barrier within said container;

(c) vapor capable of permeating through the permeable barrier;

(d) means for providing vapor at a given moment to said container, said means positioned on one side of the barrier; and (e) at least one indicator, capable of exhibiting a visual color response upon contact with said vapor, or condensed vapor, said indicator positioned on the other side of the barrier, whereby the barrier creates an induction period between the moment the vapor is introduced to said container and the moment said indicator exhibits the color response, wherein the entire observable surface of the indicator is contacted by said vapor, producing a color response over said surface substantially simultaneously, the improvement which comprises said indicator being comprised of a solution of a polydiacetylene indicating compound in a solvent therefor, said solution being capable of exhibiting a visual color response upon contact with said vapor and said vapor being soluble in said solution.

Further provided is a process for monitoring the time-temperature history of an article comprising applying to the article the device of claim 1 and providing vapor to contact the vapor-permeable barrier at the beginning of the monitoring.

Also provided is an article having the device of claim 1 applied thereto.

DESCRIPTION OF THE INVENTION AND PREFERRED EMBODIMENTS

Figure 1:
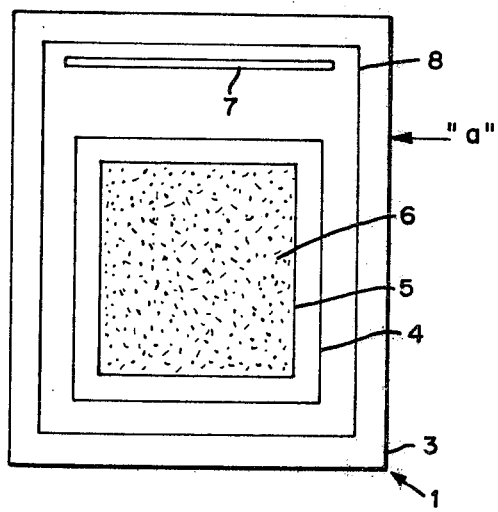
FIG. 1 is an illustration of the top view of the device containing one indicator tab and a solvent reservoir located at one end of the enclosed envelope.
Figure 2:
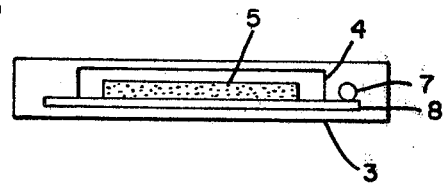
FIG. 2 is a cross-sectional side view of the above device in FIG. 1, as viewed from reference point "a".

A description of the basic invention device and a preferred embodiment, can be readily made by reference to FIG. 1 and FIG. 2. Device 1, a preferred embodiment (containing one indicator) comprises a vapor-impermeable container 3, the housing for the device, which can have an adhesive backing (not shown) for attachment to an article or to a wall or surface in the area in which the article is stored. Absorptive support 8, which acts as a support for solvent reservoir 7, is also contained in the housing as well as the sealed indicator tab comprising a compartment formed of barrier 4 enclosing indicator substrate 5 wetted with liquid indicator 6. The liquid indicator assembly, comprising a substrate and deposited liquid indicator, comprised of a polydiacetylene indicating compound and solvent therefor, is herein referred to as an "indicating tab", and when enclosed in barrier polymer 4 to form a compartment, is referred to as a "sealed indicator tab". At the beginning of the monitoring period, solvent reservoir 7, being frangible in this preferred embodiment, is ruptured, by for example, using hand pressure, thus releasing solvent which is constrained to move within vapor-impermeable container 3 and absorbed by absorptive support 8, having an affinity for the liquid solvent. Vapor forms via solvent volatilization from support 8. Formed vapor occupies the inside of container 3 and then permeates through vapor-permeable barrier 4, usually being a polymeric material, at a rate which is a function of the temperature. In this embodiment, the vapor-permeable barrier forms an enclosed compartment containing the indicator tab. After sufficient vapor has permeated through the barrier into the enclosed compartment (the amount of which is primarily dictated by the solvent and the indicating composition) to substantially contact the entire observable surface of liquid indicator 6, on indicator substrate 5, a visual color response, such as a color change from blue to yellow, occurs over the entire exposed surface of the indicator substantially simultaneously.

Knowledge of the time required, from the start of the monitoring period taken as the moment solvent is released to the container, to reach the end of the monitoring period, taken as the substantially simultaneous color response of the entire exposed surface area of the liquid indicator, reveals the effective average temperature during the monitoring period.

Knowledge of the average temperature of the monitoring period will determine the elapsed time required for development of the entire color response. A particular indicating liquid indicator/barrier/vapor system will possess a characteristic induction period (being a function of temperature) which will be known and used in a particular situation.

Figure 3:
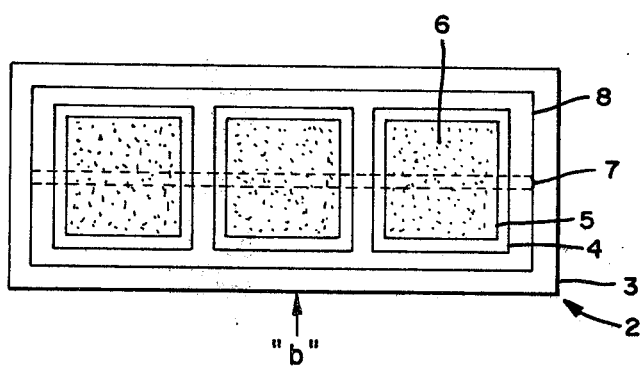
FIG. 3 is an illustration of the top view of the device containing three indicator tabs wherein the solvent reservoir is positioned below the indicator tabs in the enclosed envelope.
Figure 4:
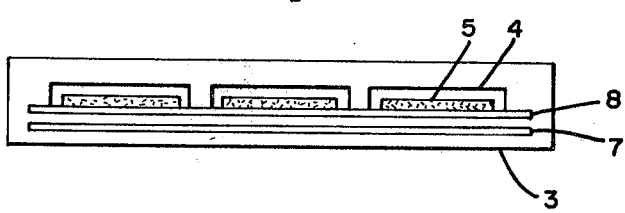
FIG. 4 is a cross-sectional side view of the above device in FIG. 3, as viewed from reference point "b".

Device 2, another preferred embodiment illustrated in FIG. 3, a top view, and FIG. 4, a cross-sectional side view, contains a plurality (here three) of indicators sealed in barrier material 4, forming sealed indicator tabs. As described above for device 1, the barrier material, used for each indicator is preferably a polymeric material, and can be the same material or different and the same thickness, permeability or different. Preferably, the overall permeability of each sealed indicator tab is different, resulting in different induction periods, thus providing the capability for measuring several different integrated time-temperature exposures in the same device. Items 1 and 3–8 for device 2 or illustrated in FIGS. 3, 4 and 5, are the same as previously identified for device 1.

Figure 5:
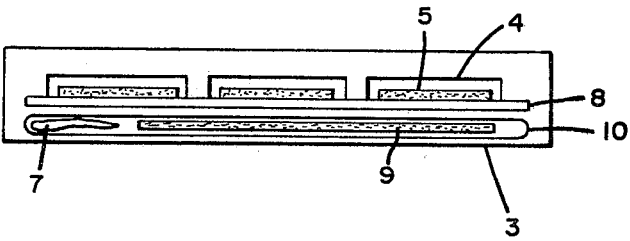
FIG. 5 is a cross-sectional side view of a modification of the device in FIG. 3 wherein the solvent reservoir is contained within solvent container 10.
Figure 6:
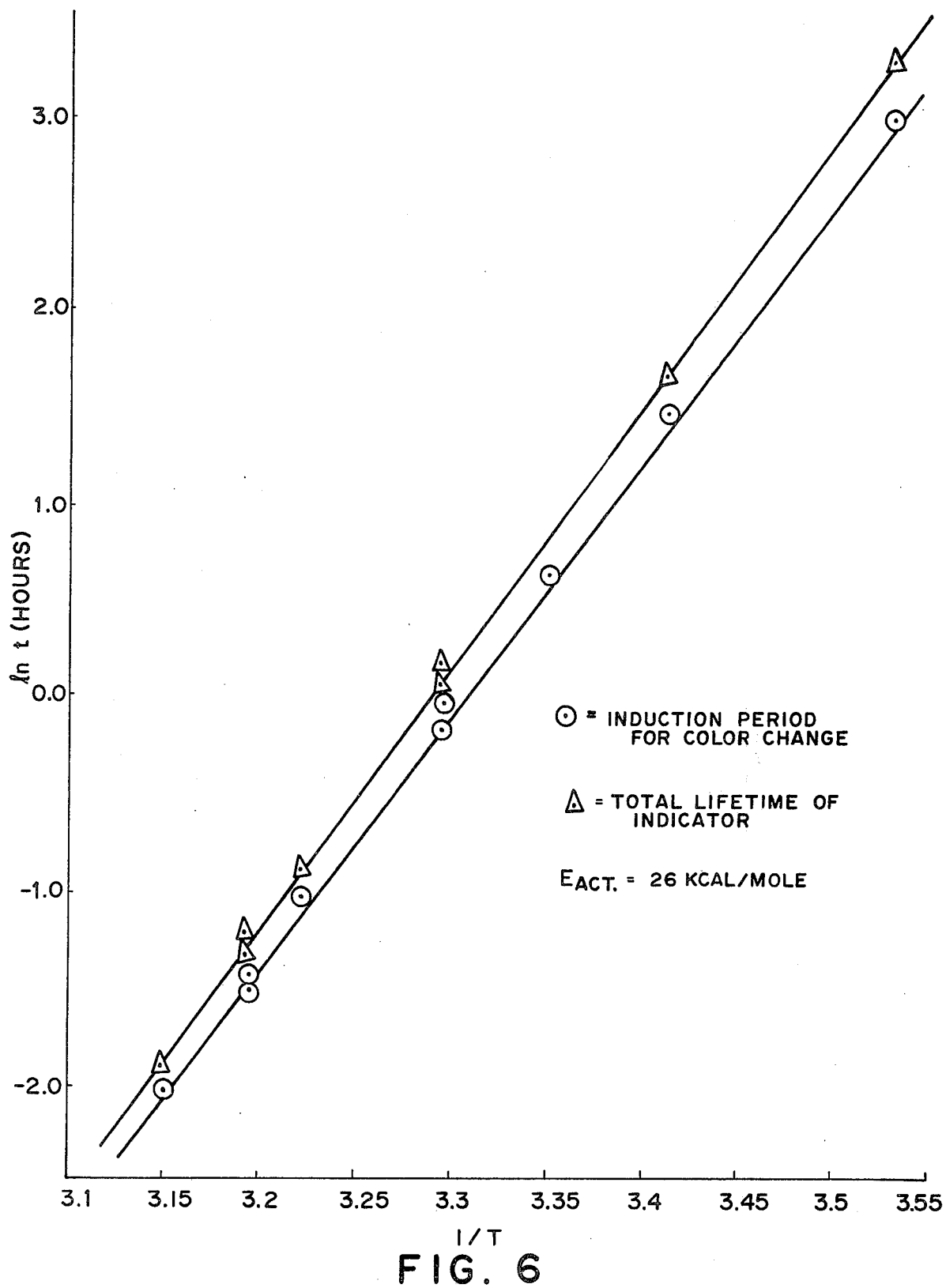

FIG. 5 is a cross-sectional side view of a further modification of the preferred basic device 2 in which solvent reservoir 7 is enclosed in a vapor-permeable non-frangible solvent container 10. In this modification, released solvent, from the rupture or solvent reservoir 7, is absorbed by solvent absorptive support 9 and vapor is formed by subsequent evaporation. Formed vapor is then constrained to permeate through container 10 prior to travel to a sealed indicator tab. By utilizing a solvent container, the overall induction period of the device can be considerably lengthened. Alternately, if the solvent container is used, the indicator need not be sealed by barrier material 4, since formed vapor is constrained to permeate through the solvent container, formed from barrier material 4, before contacting said indicator tab.

The device of this invention can be used for monitoring the time-temperature histories of perishable products over a temperature range of about −70° to +150° C. and from times ranging from about one minute to 2 years, depending on the choice of vapor, indicator and barrier materials, which will be obvious to one skilled in the art from the disclosure herein.

The function of the barrier is to create a characteristic "induction period" and "total lifetime" for a particular vapor/barrier/indicator system, such that the time required for color response to occur, after release of vapor to the system, can be predictably controlled as a function of temperature. The term "induction period", as herein used, refers to the threshold time required for the indicator to evidence a noticeable visual color response following release of vapor to the system. The term "total lifetime" as used herein, refers to the total time, following release of vapor to the system, required for the color response to attain the final value.

By the term "the barrier" is meant at least one barrier, a plurality of barriers is also contemplated in the invention device.

The barrier in the device must be positioned between the vapor and liquid indicator such that the vapor is constrained to permeate through the barrier prior to contacting the liquid indicator, such that the color response does not occur simultaneously with release of vapor to the system. In addition, the barrier must be measurably permeable to said vapor and must not be dissolved by said vapor during the monitoring period. However, a slight swelling affect of the barrier material may occur during the monitoring, and may be tolerated provided a characteristic induction period can be obtained. The barrier material may be any vapor-permeable material which is not significantly soluble in the condensed vapor and creates a measurable induction period. Such materials include natural polymers, such as leather, and synthetic polymers. Preferably, the barrier is constructed of a vaporpermeable synthetic polymer. Representative examples of useful barrier polymers include cellophane, cellulose acetate, polyethylene, polypropylene, nylon-6, nylon-66, nylon-610, polyacrylonitrile, acrylonitrile/butadiene coplymer, acrylonitrile/styrene coplymer, acrylonitrile/methyl methacrylate copolymer, acrylonitrile/methyl methacrylate/styrene copolymer, polystyrene, polyvinyl aclohol, polyoxymethylene, polyvinyl fluoride, polyvinylidene chloride, polytrifluorochloroethylene, polymethylmethacrylate, poly(4-methylpentene-1), polyethylene/polypropylene copolymer, polyethylene terephthalate, polyphenylene terephthalate, and equivalent copolymers, grafted polymers or mixtures thereof. A preferred polymer for constructing the barrier is polyethylene, preferably low density polyethylene.

The position of the barrier in the device must be such that vapor is constrained to permeate through the barrier before contacting the liquid indicator. This can be accomplished in the device in a variety of ways including: enclosing the indicator tab in a sealed compartment of barrier material; enclosing the solvent reservoir in an enclosed compartment of barrier material; enclosing both the indicator tab and solvent reservoir in barrier material; or, simply separating the vapor from the indicator in the device by a wall of barrier material, thus forming two enclosed portions of the container. In general, it is preferred to enclose the indicator tab in barrier material, thus forming an enclosed compartment.

The thickness and size of the barrier material to be employed will of course depend upon other factors as well, but usually a thickness of about 1 to 6 mils will provide excellent results for the monitoring process, with thicker sheets of barrier material resulting in longer induction periods and total lifetimes.

The permeability of the barrier material will depend strongly upon the nature of the material, discussed hereinabove, and in the case of polymeric materials, upon the crystallinity. In general, the higher the crystallinity of polymeric material, the lower the permeability of the barrier material to a particular vapor.

The container of the device is a closed vapor-impermeable structure housing the vapor, barrier and liquid indicator of the device. The container being closed, operates to contain and prevent any vapor from escaping out of the device and also to provide an observable view of the indicator tab during the monitoring period. Representative examples of suitable materials for constructing the container include polyesters, such as polyethylene terephthalate, polyamides, such as nylon 66, and polyacrylonitrile. A preferred material is nylon 66.

The size and design of the container can be varied to suit the particular article to be monitored. A limitation on the size of the device is that it must be large enough to exhibit an observable color response under the conditions of monitoring.

By the term "the liquid indicator" or "indicator" is meant at least one liquid indicator, a plurality of liquid indicators also being contemplated in the instant invention device.

The liquid indicator of the device must be capable of exhibiting a visual color response upon contacting a vapor, and must be positioned in the device on the other side of the barrier from the vapor. Upon contact with said vapor, condensed vapor, the liquid indicator undergoes a color response, preferably a color change, over its entire exposed surface substantially simultaneously, such that the color response is essentially uniform and no localized moving colored boundaries are present. The reason as to why the liquid indicator, comprised of a polydiacetylene indicating compound dissolved in a suitable solvent, undergoes a color response upon contacting with said vapor is not clearly understood and may be due to a variety of mechanisms such as precipitation of the indicating compound from solution, production of a new conformation of said indicating compound in solution, production of a new hydrogen-bonded species of said compound in solution, or the like. Regardless of the mechanism underlying the color response, the incorporation of a vapor-indicator combination into the device system is not specifically directed or predicated upon one particular mechanism, but is based generally upon the observed fact that a liquid indicator is capable of undergoing a color response upon contact with a vapor or condensed vapor.

The characteristic induction period for the device of this invention is lengthened by the use of a liquid indicator system, in which a solution of indicating compound in a suitable solvent, can be employed individually or preferably contacted with a substrate to form a wetted substrate, generally saturated with said solution. The reason why the induction period for the device in this improved modification is lengthened over the induction period of the prior art utilizing solid indicator systems is not clearly understood. The answer may be that a higher concentration of diffusing vapor is required for a color transition in the present liquid indicator system.

The indicator comrises a polydiacetylene indicating compound dissolved in a suitable solvent, in solution, and preferably contacted with a substrate, wherein the substrate is wetted with said solution. The substrate can be any solid porous material which acts as a support for the compound in solution during the monitoring process and in the simplest embodiment can be the surface of the barrier material or the surface of the container. It is preferred, however, to use a separate flexible support such as filter paper. The solution of indicating compound can be contacted with the substrate by means of immersing, spraying or the like.

The indicating compounds of the improved invention device are polydiacetylene componds, or mixtures thereof, formed from diacetylene monomers containing at least one conjugated diyne group (i.e., —C≡C—C≡—) per molecule. Polydiacetylene compounds are known in the art, including methods of preparation, and are adequately described in U.S. Pat. No. 3,999,499 (Patel et al. to Allied Chemical, 1976) which is hereby incorporated by reference. The polydiacetylene compounds contain at least one substituent (R or R') below typically selected from the group consisting of alkyl, aryl, sulfonate, urethane and alcohol derivatives and preferably the polydiacetylene containes two urethane substituents. Representative examples include those of the formula:

$$RNHCO—O—(CH_2)_n—C≡C—C≡C—(CH_2)_m—O—CONHR'$$

where n and m are integer values and can be the same or different and are at least 1; and preferably 1-4; and wherein R and R' can be the same or different and are alkyl, aryl, sulfonate, urethane and alcohol derivatives.

Representative polydiacetylenes of the above formula useful in the instant invention include those formed from monomers in the listing below, where n=m, R=R' and descriptive shorthand chemical names are given:

| n,m | R,R' | Descriptive Name |
|---|---|---|
| 2 | $C_2H_5$ | ODEU |
| " | meta chlorophenyl | ODDmCPU |
| " | $(CH_2)_3CH_3$ | ODDnBU |
| 3 | $CH_3$ | 3DMU |
| " | ortho chlorophenyl | 3DoCPU |
| " | phenyl | 3DPU |
| " | $C_2H_5$ | 3DEU |

| n,m | R,R' | Descriptive Name |
|---|---|---|
| 4 | $CH_3$ | 4DMU |
| " | $C_2H_5$ | 4DEU |
| " | $-CH_2CH_2Cl$ | 4D2CEU |
| " | ortho chlorophenyl | 4DoCPU |
| " | meta methoxyphenyl | 4DmMPU |
| " | para chlorophenyl | 4DpCPU |
| " | meta tolyl | 4DmTU |

Preferred polydiacetylenes in the invention are those produced from monomeric diacetylenes wherein R and R' independently have the formula:

$$XO-CO-(CH_2)_a-$$

wherein X is linear or branched $C_1$–$C_{18}$ alkyl; and a is an integer value from 1–4. Particularly preferred polydiacetylenes are those derived from diacetylenes of the above formula wherein m and n are the same and either 3 or 4; a is one; and R and R' are the same and X is either ethyl or n-butyl. Representative examples of this class are: 4,6-decadiyn-1,10-diol bis (ethoxycarbonylmethylurethane), 3DECMU, 4,6-decadiyn-1,10diol bis(n-butoxycarbonylmethylurethane), 3DBCMU, 5,7-dodecadiyn-1,12-diol bis(ethoxycarbonylmethylurethane), 4DECMU, and 5,7dodecadiyn-1,12-diol bis(n-butoxycarbonylmethylurethane), 4DBCMU.

Solvents for the indicating compounds of this invention include those which are good solvents for the compound, are chemically inert under the conditions of the moitoring, do not significantly dissolve the materials of construction of the container, and have boiling points of at least about 25° C. at atmospheric pressure. Representative examples of classes of solvents include $C_3$14 $C_6$ alkyl ketones, halogenated $C_1$-$C_4$ alkanes, containing 1 to 4 halogen atoms, $C_3$-$C_6$ N,N-dialkylalkanoamides, $C_1$-$C_3$ monohydric alkyl alcohols, $C_1$-$C_5$ saturated alkanoic monocarboxylic acids, or lower alkyl esters thereof, $C_1$-$C_4$ nitroalkanes, $C_2$-$C_6$ alkyl sulfoxides, $C_2$-$C_6$ alkyl ethers, cyclic $C_4$-$C_6$ alkyl ethers, $C_7$-$C_9$alkylphenols, $C_5$-$C_{10}$ heterocyclic nitrogen compounds, phenol, water, trihaloacetic acids, trihalo $C_1$-$C_4$ alkyl alcohols, equivalents or mixtures thereof. Specific examples include methyl ethyl ketone, dichloromethane, chloroform, carbon tetrachloride, dimethyl sulfoxide, N,N-dimethylformamide, N,N-dimethylacetamide, methanol, ethanol, isopropanol, acetic acid, water, p-dioxane, p-cresol, phenol, pyridine, ethyl acetate, nitromethane, dimethylsulfoxide and trifluoroacetic acid. Preferred solvents are chloroform, dimethylsulfoxide, dimethylformamide and trifluoroacetic acid.

In general, solutions of indicating compounds in solvent of about 0.01 to about 50 percent compound by weight of solution are used and preferably solutions of about one percent compound by weight of solution are used.

The liquid indicators display a variety of color changes when contacted with a vapor. For example, a one weight percent solution of poly 3DECMU in dimethylformamide is yellow and turns to a blue color upon contacting chloroform or acetone vapor. Conversely, a blue solution of poly 3DBCMU in chloroform/hexane solution turns yellow upon contacting with trifluoroacetic acid. Both types of color responses can be utilized in the invention device for monitoring time-temperature histories of articles.

Vapor in the present invention device is positioned such that it is constrained to permeate through the barrier before contacting the indicator. The vapor must be able to permeate through the barrier without significantly dissolving said barrier, must be reactive with the compound to produce a color response, must be soluble in the solution of compound and preferably the vapor in the condensed liquid state has a boiling point of greater than 25° C. at atmospheric pressure.

Vapor in the device acts to produce a color response upon contact with said liquid indicator. The mechanism of how the color response occurs is not clearly understood and is probably different depending upon the particular vapor used. For example, as described above, poly 3DECMU in DMF solution, when contacted with chloroform or acetone vapor, which are known non-solvents for poly 3DECMU, results in a solution color change from yellow to blue. Formation of intermediate conformational structures having different solubilities and colors may be involved. Conversely, a solution of poly 3DBCMU in chloroformhexane, when contacted with a halogenated alkanoic acid, such as trifluoroacetic acid, a known hydrogen-bonding agent, results in a color change from blue to yellow. The color change here is thought to be due to the interference in the intramolecular hydrogen bonding of the compound in solution, causing new hydrogen-bonded structures which exhibit different absorption spectra and thus, a correspondingly different observed color. By the term "non-solvent", as used herein, is meant that the dissolved indicating compound can be precipitated upon contacting vapor of the non-solvent.

Representative examples of vapor useful in the instant invention include $C_3$-$C_6$ linear or branched acyclic alkyl ketones; halogenated $C_1$-$C_3$ alkanes, containing 1–4 halogen atoms being fluorine, chlorine, bromine, iodine or mixtures thereof halogenated $C_1$-$C_3$alkanoic acids containing 1–4 halogen atoms being fluorine, chlorine, bromine, iodine or mixtures thereof; $C_3$-$C_6$ N,N-dialkylalkanoamides, wherein said alkyl groups may be the same or different and may be linear or branched; $C_1$-$C_3$ monohydric alkyl alcohols; $C_1$-$C_4$ saturated alkanoic monocarboxylic acids, wherein said alkane portions may be either linear or branched; $C_2$-$C_6$ alkyl sulfoxide and $C_2$—$C_6$ alkyl ethers, wherein said alkyl groups may be the same or different and may be linear or branched; cyclic $C_4$—$C_9$ alkyl ethers, said alkyl groups being either linear or branched; $C_7$—$C_9$ alkylphenols, said alkyl groups being either linear or branched and said phenol being either mono-, di- or trisubstituted; $C_5$-$C_{10}$ heterocyclic nitrogen compounds, containing up to 2 ring nitrogen atoms, and 1 or 2 aromatic rings, being fused or separated; phenol, trihaloacetic acids, water, equivalents of the above-recited compounds or mixtures thereof. Preferred vapors for use in the invention device are those which act as a non-solvent for the compound in solution, or as a hydrogen-bonding agent for the compound in solution. Vapors which satisfy these criteria will be obvious to one skilled in the art from this disclosure. Illustrative of particular preferred vapors are acetone, methl ethyl ketone, dichloromethane, chloroform, carbon tetrachloride, dimethyl sulfoxide, dimethylformamide, dimethylacetamide, methanol, ethanol, isopropanol, acetic acid, water, p-dioxane, p-cresol, phenol, pyridine, trifluoroacetic acid, trichloroacetic acid, equivalents or mixtures thereof.

Means for providing vapor to the container at the beginning of the monitoring process, i.e. at a given moment, is positioned at the other side of the barrier from the indicator and is usually a frangible solvent reservoir. The reservoir being frangible, is easily ruptured as for example by hand pressure at the beginning of the monitoring period. The solvent is allowed to volatize to form vapor, usually by wetting an absorptive support, e.g., a porous substrate, such as filter paper, which facilitates the evaporation process. The solvent reservoir can be constructed of a variety of materials with the proviso that the material is not significantly soluble in the solvent, but may be slightly swelled during the monitoring process. In one embodiment, the material is sufficiently non-permeable to the solvent that escape of solvent to the container does not occur prior to the desired monitoring period, as illustrated in FIG. 1. Representative materials that can serve as the solvent reservoir include thin-walled glass, aluminum foil and frangible but vaporimpermeable plastics. A preferred material is thin-walled glass.

In another embodiment, as illustrated in FIG. 5, the solvent reservoir 7 is contained within a non-frangible solvent container 10 along with solvent absorptive support 9. In this embodiment the solvent reservoir is frangible and is constructed from materials described above. The solvent container 10 is constructed from barrier material as described herein.

Absorptive support 8 and solvent absorptive support 9 usually are constructed of the same materials although they could be different depending upon the specific circumstances. The purpose of support 9 is to provide an absorbant surface from which vapor is easily formed in the solvent container. The purpose of support 8 is to support the solvent reservoir and/or the indicating tab, provide a background to make easier visual observation of the color response, and to provide a surface from which vapor can easily be formed. Representative examples of materials include filter paper, cotton, and absorptive tissue. Preferred material is filter paper.

A preferred device of the invention is that illustrated in FIG. 1 wherein the liquid indicator is comprised of polymerized 4,6-decadiyn-1,10-bis(ethoxycarbonylmethyl-urethane), poly 3DECMU, as indicating compound dissolved in dimethylformamide; barrier material of polyethylene, preferably low density polyethylene; and wherein the vapor is chloroform, acetone, or trifluoroacetic acid.

The energy of activation of the device, $E_{act}$, can be calculated by measuring the iduction period or the total lifetime of the device during operation at two or more temperatures. The energy of activation of the device is a measure of the change in rate (i.e., rate of color change or development in the present devices) with temperature. The natural logarithm of the induction period, (ln t) as the ordinate is plotted versus the inverse absolute temperature $1/T$ as the abscissa and the energy of activation is calculated from the slope of the resulting straight line plots, by known methods in the art. In general, devices having higher energies of activation, will undergo color responses at relatively greater rates, at higher temperatures, as compared with the rates at lower temperatures than for devices having lower activation energies.

Also provided in the instant invention is a process for monitoring the time-temperature history of an article comprising applying to the article the improved device of this invention and providing vapor to contact the vapor-permeablebarrier at the beginning of the monitoring period. The device contains a means by which it can be readily attached to an article to be monitored, preferably via an adhesive backing. Means for providing vapor to the device are discussed hereinabove and can be a frangible solvent reservoir. The monitoring process can be conducted at a temperature of about $-70°$ to $+150°$ C.; at atmospheric pressures and even at reduced pressures in partial vacuum.

Also a part of the instant invention is an article having the device of the invention, as described herein, attached thereto. Such articles include frozen foods, blood plasma, perishable vaccines, photographic film and the like.

The nature of the container, barrier, liquid indicator, vapor and means for providing vapor to the device are fully and adequately described hereinabove. As described in Example 1, the indicating tab can be prepared by contacting the substrate with a solution of the indicating compound such as by immersion. Alternately, the indicating compound may be dispersed in a medium such as a binder and applied to the substrate. The indicating tab can then be sealed in a barrier material such as a polymer, by means of a sealer, such as a hot press sealer, glues and pressure sensitive adhesives. Preferred is a hot press sealer. The other components of the device, including the solvent reservoir 7 (containing solvent) and absorptive supports 8 and 9, are also sealed in the container by means of the sealer to form the completed device.

The following examples are illustrative of the best mode of carrying out the invention, as contemplated by us, but should not be construed to be limitations on the scope or spirit of the instant invention. Parts are by weight where given unless otherwise indicated.

EXAMPLE 1

Preparation of the Device

The device was prepared in the following general manner: (1)a solid, poly-3DECMU, was dissolved in a suitable solvent, DMF, forming about a 1% by weight slution; (2) a 1×"1× square piece of filter paper (Whatman No. 1) was immersed in the solution to thoroughly saturate the filter paper and then the wetted paper was sealed in a 1.2"×1.2" piece of vapor-permeable polymer, either low-density polyethylene or poyethylene terephthalate of varying thickness, being either 2 or 6 mil thick. The sealed indicators were then placed into a container of 3.8"×1.5" vapor-impermeable material, in this case, nylon-66. A vapor source, in this case, a 3.6"×1.2" piece of filter paper wetted with either chloroform or acetone was also placed into the container and the container sealed with a heat sealer. The starting time for monitoring a time-temperature history, i.e., the start of the measurement, was taken as the moment the outer envelope was completely sealed. The threshold time required for a visually observable color change to developed, i.e., the "color response", is referred to as the "induction period." The values of the induction periods for the different indicators prepared are listed below in Table 1. The visual color response that was noted was a change in color from yellow to blue and thus the start and completion of the color change and the length of the induction period were readily ascertainable. The total lifetime of the indictor tab, i.e., the total time required for the indicator in the tab to completely undergo the color change from start to finish, in this case from yellow to blue, was also visually determined, at about 25° C.

TABLE I

| Vapor | Barrier Composition | Thickness of the Barrier (mil) | Induction Period (hrs) yellow → blue | Total Lifetime (hrs) |
|---|---|---|---|---|
| Chloroform | Polyethylene | 2 | 0.6 | 0.82 |
|  | polyethylene | 6 | 2.1 | 2.9 |
|  | Polyester | 2 | 0.1 | 0.16 |
| Acetone | Polyethylene | 2 | 32 | 42 |
|  | Polyethylene | 6 | 106 | 144 |
|  | Polyester | 2 | 5 | 7 |

As can be seen from the above data, the induction period and the total lifetime of the indictor can be varied by (1) varying the barrier composition, (2) varying the thickness of the barrier, and (3) varying the vapor composition,

EXAMPLE 2

Use of Hydrogen-Bonding Agent as Vapor

The device utilized in this example was essentiallly the same as that described in Example 1. The indicator solution was a purple 0.6 weight percent solution of poly 3DBCMU in $CHCL_3$:hexane, the barrier polymer 6 mil thick low-density polyethylene and the vapor/liquid used was trifluoroacetic acid. Device operation was conducted at room temperature during which a purple to yellow color transition was observed. Results are listed below in Table II.

TABLE II

| Barrier Composition | Thickness of the Barrier (mil) | Induction Period (hrs) purple → yellow | Total Lifetime (hrs) |
|---|---|---|---|
| Polyethylene | 6 | 11.0 | 14 |

As can be seen from the above example, the color transition can be reversed by using a hydrogen-bonding agent as the vapor.

EXAMPLE 3

Use of Poly 4DBCMU as Indicating Compound in Solution

The device used in this example was essentially identical to that of Example II except that a red b 2 weight percent solution of poly 4DBCMU in chloroform/hexane was the indicating solution and trifluroacetic acid was the vapor used. Device operation was conducted at room temperature and the results are listed in TABLE III.

TABLE III

| Barrier Composition | Thickness of the Barrier (mil) | Induction Period (hrs) red → yellow | Total Lifetime (hrs) |
|---|---|---|---|
| Polyethylene | 6 | 3.1 | 4.8 |

As can be seen from the above examples, a desired color transition, i.e., blue to yellow, yellow to blue, red to yellow, or yellow to red, can be obtained by selecting a suitable polydiacetylene and vapor combination, which will be obvious to one skilled in the art from this disclosure.

We claim:

1. In a device for monitoring the time-temperature history of an article including:
   (a) a closed vapor-impermeable container;
   (b) at least one vapor-permeable barrier within said container;
   (c) vapor capable of permeating through the permeable barrier;
   (d) means for providing vapor at a given moment to said container, said means positioned on one side of the barrier; and
   (e) at least one indicator, capable of exhibiting a visual color response upon contact with said vapor or condensed vapor, said indicator positioned on the other side of the barrier, whereby the barrier creates an induction period between the moment the vapor is introduced to said container and the moment said indicator exhibits the color response, wherein the entire observable surface of the indicator is contacted by said vapor, producing a color response over said surface entire surface substantially simultaneously, the improvement which comprises said indicator being comprised of a solution of a polydiacetylene indicating compound in a solvent therefor, wherein said solution being capable of exhibiting a visual color response upon contact with said vapor, and said vapor being soluble in said solution.

2. The improvement according to claim 1 wherein said indicator further comprises a substrate wetted with said solution.

3. The improvement according to claim 1 wherein said polydiacetylene is formed by polymerizing a monomer of the following formula:
   $$RNHCO-O-(CH_2)_n-C{\equiv}C-C{\equiv}C-(CH_2)_m-O-CONHR'$$

wherein n and m are integer values and can be the same or different and are at least 1, wherein R and R' can be the same or different and are selected from the group consisting of alkyl, aryl, sulfonate, urethane and alcohol derivatives.

4. The improvement according to claim 3 wherein said R and R' radicals independently have the formula:

$$XO-CO-(CH_2)_a-$$

wherein X is linear or branced $C_1-C_{18}$alkyl, and a is an integer value from 1-4.

5. The improvement according to claim 4 wherein said polymer is characterized in that m and n are the same and either 3 or 4; a is one; and R and R' are the same and X is either ethyl or butyl.

6. The improvement according to claim 1 wherein said solvent has a boiling point of at least about 25° C. at atmospheric pressure.

7. The improvement according to claim 1 wherein said solution contains about 0.01 to about 50 percent by weight of said compound.

8. The improvement according to claim 1 wherein said vapor is a non-solvent for the compound in solution.

9. The improvement according to claim 1 wherein said vapor is a hydrogen-bonding agent for the compound in solution 10. A process for measuring the time-temperature history of an article comprising applying to the article the device of claim 1 and providing vapor to contact said vaporpermeable barrier at the beginning of the monitoring